United States Patent [19]

Lilly

[11] Patent Number: 5,131,565

[45] Date of Patent: Jul. 21, 1992

[54] TONGUE DEPRESSOR DISPENSER

[76] Inventor: Cary Lilly, 380 Roselawn Dr., Clarksville, Tenn. 37042

[21] Appl. No.: 662,240

[22] Filed: Feb. 20, 1991

[51] Int. Cl.⁵ .............................................. B65H 3/00
[52] U.S. Cl. ................................... 221/270; 221/274; 221/276; 221/250
[58] Field of Search ............... 221/268, 270, 272, 274, 221/276, 287, 197, 250

[56] References Cited

U.S. PATENT DOCUMENTS

| | | | |
|---|---|---|---|
| 1,719,826 | 7/1929 | Aldrich | 221/274 |
| 2,015,628 | 9/1935 | Karai | 221/276 |
| 2,467,799 | 4/1949 | Archer | 221/197 |
| 2,551,425 | 5/1951 | Drexel | 221/276 |
| 2,560,327 | 7/1951 | Bergman | 221/276 |
| 3,790,027 | 2/1974 | Barnhart | 221/274 |

FOREIGN PATENT DOCUMENTS 2502626 7/1976 Fed. Rep. of Germany ...... 221/197

Primary Examiner—H. Grant Skaggs
Attorney, Agent, or Firm—Stephen T. Belsheim

[57] ABSTRACT

A tongue depressor dispenser having a support base to which an upper cover detachably mounts. A dispenser assembly mounts to the support base. The dispenser assembly includes an ejector assembly that is movable to dispense a single tongue depressor at a time.

6 Claims, 2 Drawing Sheets

TONGUE DEPRESSOR DISPENSER

BACKGROUND OF THE INVENTION

The present invention relates to dispensing devices. More specifically, the present invention relates to dispensing devices for dispensing tongue depressors.

The medical profession frequently use tongue depressors. Most hospitals and physicians offices use tongue depressors. The medical professional typically stores tongue depressors in a jar with a lid, or in a storage box for shipment as provided by the manufacturer. For example, a physician's examining room often times contains a jar of tongue depressors.

Although jars or boxes can adequately store tongue depressors, they do not provide for or maintain the aseptic integrity of the depressors. Each time one needs a tongue depressor the box or jar must be opened and the hand inserted to grasp a single depressor. This leads to the contamination of the entire stock of tongue depressors.

In some situations, the shipment box is used to store the tongue depressors. When this happens, the top of the box is removed which contaminates the entire stock of depressors. As can be appreciated, the contamination of the entire stock or supply of depressors is an undesirable result. It would be desirable to provide a device for dispensing tongue dispensers which maintains the aseptic integrity of the depressors.

Although jars adequately store tongue depressors, they are sometimes cumbersome to use. For instance, if there is a medical emergency, the time needed to perform the steps of removing the lid and reaching into the jar to grasp a tongue depressor can become critical. It would be desirable to provide a device for dispensing tongue depressors which conveniently, efficiently, and aseptically stores and dispenses tongue depressors.

SUMMARY OF THE INVENTION

A principal object of the invention is provide a tongue depressor dispenser with aseptic valve.

Another object of the invention is to provide a tongue depressor dispenser that aseptically, conveniently, and efficiently stores tongue depressors.

Finally, it is still another object of the invention to provide a tongue depressor dispenser that aseptically, conveniently and efficiently dispenses tongue depressors.

In one form thereof, the invention is a tongue depressor dispenser comprising a housing including a support base and a cover. A dispenser assembly mounts to the support base. The dispenser assembly includes an ejector assembly which mounts to the support base and operatively connects to a lever. The lever is movable to a condition wherein the ejector assembly dispenses a tongue depressor. A storage chamber receives a plurality of stacked tongue depressors contained in a box.

In another form thereof, the invention is a tongue depressor dispenser comprising a housing including a support base and a cover. The support base includes a bottom member which contains an elongate slot and a front wall which contains an exit aperture and a lever aperture. An ejector assembly mounts to the underneath surface of the bottom member. The ejector assembly includes a movable pusher having an upstanding portion thereof protruding through the slot. A lever mounts to the support base and protrudes through the lever aperture. The lever operatively connects to the pusher. The lever is movable between one of two conditions wherein when in a first condition, the pusher does not engage a tongue depressor, and when in a second condition, the pusher engages a tongue depressor so that a portion of the tongue depressor protrudes through the exit aperture. A plurality of tongue depressors in a stacked condition are over the slot such that the pusher engages the bottom most depressor upon the movement of the lever from the first to the second condition.

In still another form thereof, the invention is a tongue depressor dispenser for dispensing a single depressor from a covered stack of depressors. The dispenser comprises a housing including a support base. The support base includes a bottom member containing an elongate slot and a front wall containing an exit aperture. An ejector assembly mounts to the underneath surface of the bottom member. The ejector assembly includes a forward mounting member and a rearward mounting member which mount to the underneath surface of the bottom member. A rod extends between the mounting member. A pusher slidably mounts to the rod and has an upstanding portion protruding through the slot. A spring is sandwiched between the pusher and the forward mounting member. A lever operatively connected the pusher is movable between a first condition of the ejector assembly wherein the pusher does not engage a tongue depressor and a second condition of the ejector assembly wherein the pusher engages a tongue depressor so that a portion of the tongue depressor protrudes through the exit aperture. The spring biases the ejector assembly to the first condition. A storage chamber wherein a plurality of tongue depressors are in a single stack over the slot such that the pusher engages the bottom most depressor upon the movement of the lever from the first to the second condition.

DETAILED DESCRIPTION OF A SPECIFIC EMBODIMENT

Figure 1:
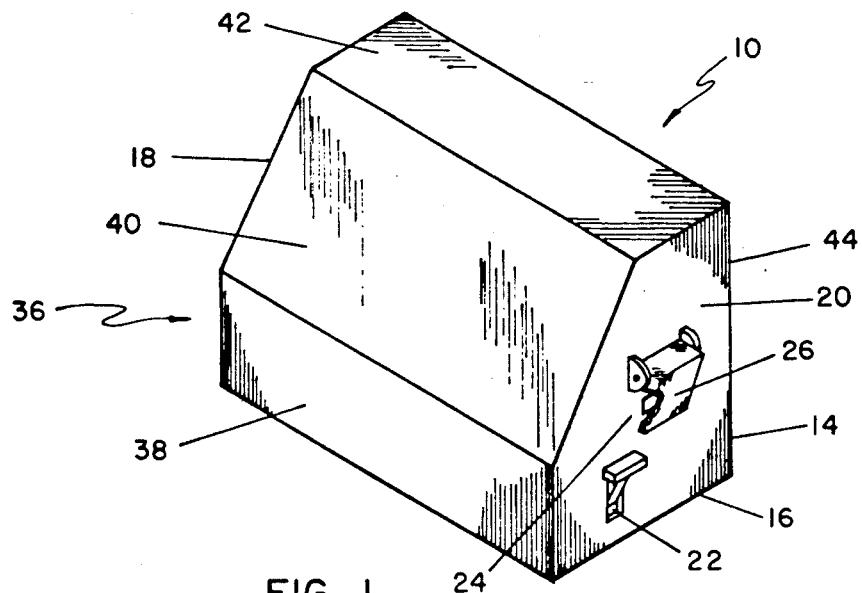
FIG. 1 is a perspective view of a specific embodiment of the tongue depressor dispenser of the invention.

Referring to the drawings, FIG. 1 illustrates a specific embodiment of the dispenser of the present invention 10. Dispenser 10 includes a support base 14. Support base 14 has a bottom 16 and opposite side walls 18, 20. The forward wall 20 contains a pair of apertures 22 and 24. A hinged cover 26 selectively covers aperture 24. Applicant will explain the purpose of these apertures 22, 24 in more detail hereinafter. Support base 14 further includes a floor 28 vertically disposed above bottom 16. Floor 28 contains an elongate slot 32 therein. Slot 32 aligns with aperture 24.

Dispenser 10 further includes a cover. Cover 36 has a short vertical wall 38, a sloped wall 40, a removable top wall 42, and a long vertical wall 44. Cover 36 extends upward from support base 14. However, cover 36 may mount or attach to support base 14 in a variety of conventional mechanical attachments. Top 42 is removable to provide access to the storage chamber. Although not illustrated top 42 could include a lip which overhangs the adjacent surfaces, 18, 20, 40, and 44. Further, top 42 could include indintations which would help a user grasp top 42 thereby aiding the removal and replacement top 42.

Dispenser 10 further includes an ejector assembly 50. Ejector assembly 50 includes a forward mounting member 52 and a rearward mounting member 54. Each mounting member (52, 54) affixes to the bottom surface of floor 28 so as to depend therefrom. A rod 56 extends between the mounting member 52 and 54. A pusher 58 slidably mounts to rod 56 so as to be slidable thereon. Pusher 58 has a pair of lower extensions 60, each of which contain an aperture which receives the rod 56. Pusher 58 has an upwardly extending engagement portion 62 which protrudes through slot 32 in floor 28. A spring 64 mounts to rod 56 between the forward lower extension 60 and the forward mounting member 52. A lever 68 pivotally mounts to support base 14 so that a portion thereof extends through aperture 22. A wire or cable 70 joins lever 68 to the forward lower extension 60 of the pusher 58.

In operation, the dispenser 10 aseptically, conveniently and efficiently dispenses a single tongue depressor 72 from a stack of a plurality of tongue depressors 72 contained in a box 74. Box 74 is open at its bottom to provide access for the pusher 58 to engage a depressor.

Figure 2:
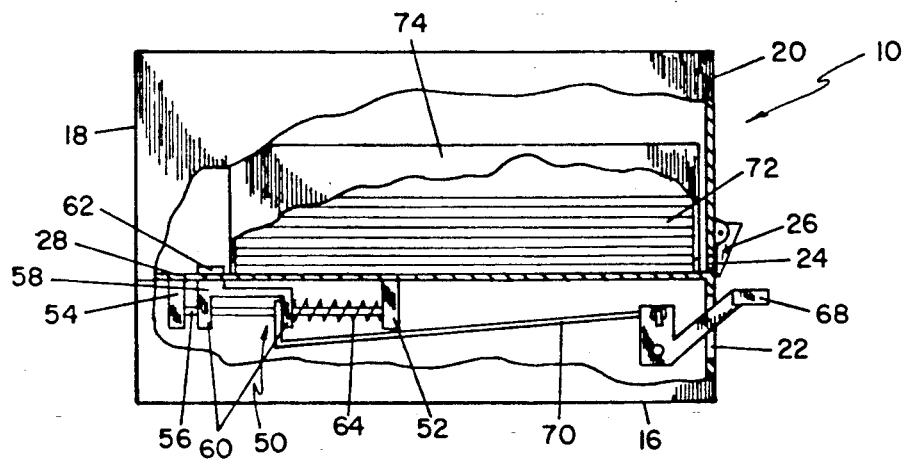
FIG. 2 is a side view of the embodiment of FIG. 1 with a portion of the housing cut away to illustrate the interior of the dispenser wherein the ejector assembly does not engage a depressor.
Figure 3:
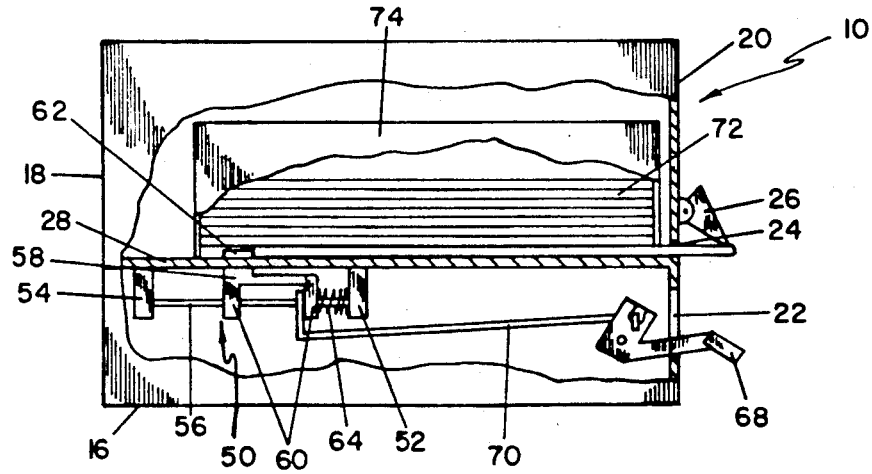
FIG. 3 is a side view of the embodiment of FIG. 1 with a portion of the housing cut away to illustrate the interior of the dispenser wherein the ejector assembly engages a depressor.

Referring to FIG. 2, the dispenser 10 is in a condition wherein the engagement portion 62 of pusher 58 does not engage the bottommost tongue depressor 72. Spring 64 biases pusher 58 into a rearward position which corresponds to this condition. This is the condition in which the dispenser 10 exists when not dispensing a depressor.

When one desires to dispense a tongue depressor 72, one pushes down on the lever 68. Lever 68 pivots in a downward direction which causes wire 70 to pull on pusher 58. Pusher 58 slides in a forward direction on rod 56 against the bias of spring 64. As pusher 58 slides forward, the engagement portion 62 engages the rearward end of the bottommost tongue depressor 72 so as to push the depressor 72 along with the forward movement of pusher 58.

Figure 4:
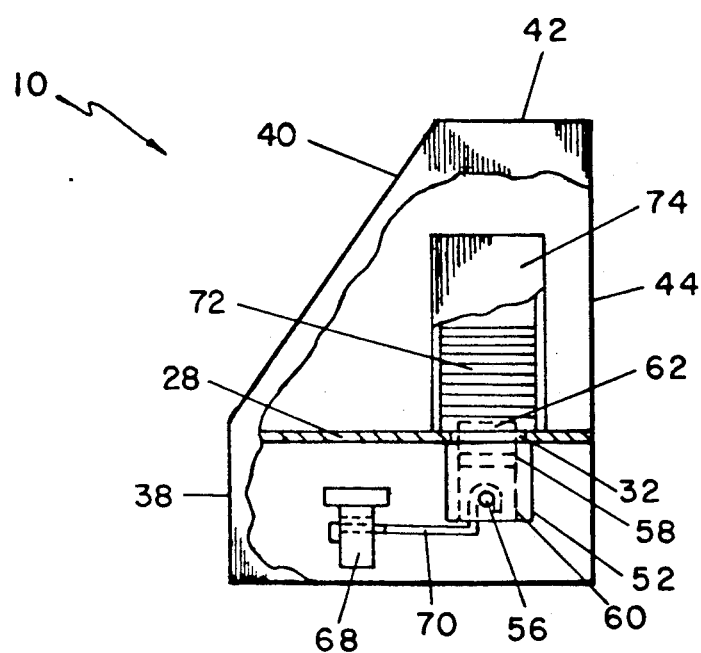
FIG. 4 is a front view of the embodiment of FIG. 1 wherein a portion of the housing is cut away to illustrate the relationship between the ejector assembly and the tongue depressors.

FIG. 4 illustrates the condition of the dispenser 10 upon the pusher 58 reaching the end of its forward travel. The forward end of the tongue depressor 72 engages the cover 24 to pivot it out of the way. The forward end of the depressor 72 projects out of the dispenser 10 through aperture 24. One can now grasp the tongue depressor 72 and put it to its intended use.

Upon the conclusion of the dispensing operation, one lets up on the lever 68. The biasing force of spring 64 causes pusher 58 to return to its original position in which it does not engage a depressor 72. The dispenser 10 is ready to again dispense a single depressor 72.

What is claimed is:

1. A tongue depressor dispenser comprising:
   a housing including a support base and a removable cover;
   a dispenser assembly mounted to said support base;
   said dispenser assembly including:
      an ejector assembly mounted to the support base and operatively connected to a lever, said lever being movable to a condition wherein the ejector assembly dispenses a tongue depressor;
      a storage chamber receives a plurality of tongue depressors in a stacked condition;
      a support base having a bottom member with an underneath surface containing a slot; and
   said ejector assembly includes forward and a rearward mounting members mounted to the underneath surface of the bottom member, a rod extends between said mounting members, a pusher is slidably mounted to the rod and has an engagement portion thereof protruding through the slot wherein the engagement portion engages the depressor to be dispensed.

2. The tongue depressor dispenser of claim 1 wherein said ejector assembly further comprises a spring positioned on the rod between the pusher and the forward mounting member so as to exert a biasing force to bias the ejector assembly to a condition wherein the pusher does not engage a depressor.

3. The tongue depressor dispenser of claim 1 wherein the front wall contains an exit aperture through which a depressor protrudes when dispensing and a lever aperture through which the lever protrudes.

4. The tongue depressor dispenser of claim 1 wherein the dispensors are in a container, the container being positioned so that the tongue depressors are stacked over the slot whereby the bottom depressor is engaged by the ejector assembly upon movement of the lever to the dispensing condition.

5. A tongue depressor dispenser for dispensing a single depressor from a covered stack of depressors, the dispenser comprising:
   a housing including a support base, said support base including a bottom member containing an elongate slot and a front wall containing an exit aperture;
   an ejector assembly mounted to the underneath surface of the bottom member, said ejector assembly including a forward mounting member and a rearward mounting member mounted to the underneath surface of the bottom member, a rod extending between said mounting members, a pusher slidably mounted to the rod and having an upstanding portion protruding through the slot, a spring being sandwiched between the pusher and the forward mounting member, a lever operatively connected to said pusher and being movable between a first condition of the ejector assembly wherein the pusher does not engage a tongue depressor and a second condition of the ejector assembly wherein the pusher engages a tongue depressor so that a portion of the tongue depressor protrudes through the exit aperture, the spring biasing the ejector assembly to the first condition;
   a storage chamber wherein a plurality of tongue depressors are in a stack over the slot such that the bottom most depressor is engaged by the pusher upon the movement of the lever from the first to the second condition.

6. The dispenser of claim 5 wherein the cover further includes a removable top for access to storage chamber.

* * * * *